(12) United States Patent
Hu et al.

(10) Patent No.: US 10,942,105 B1
(45) Date of Patent: Mar. 9, 2021

(54) EXPERIMENTAL DEVICE FOR CARBON DIOXIDE IMBITION, DIFFUSION AND OIL DISCHARGE IN TIGHT OIL RESERVOIR

(71) Applicant: Southwest Petroleum University, Chengdu (CN)

(72) Inventors: Shuyong Hu, Chengdu (CN); Tao Long, Chengdu (CN); Xiaobing Han, Chengdu (CN); Yulong Zhao, Chengdu (CN); Huiying Tang, Chengdu (CN); Xindong Wang, Chengdu (CN); Nana Song, Chengdu (CN); Xueqiang Guo, Chengdu (CN); Tingting Qiu, Chengdu (CN); Bingyang Zheng, Chengdu (CN); Xinyuan Long, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 0 days.

(21) Appl. No.: 17/037,635

(22) Filed: Sep. 29, 2020

(30) Foreign Application Priority Data

Dec. 31, 2019 (CN) .......................... 201911420943.9

(51) Int. Cl.
*G01N 13/00* (2006.01)
*G01N 33/24* (2006.01)
*E21B 49/02* (2006.01)

(52) U.S. Cl.
CPC ........... *G01N 13/00* (2013.01); *G01N 33/241* (2013.01); *E21B 49/02* (2013.01); *G01N 2013/003* (2013.01)

(58) Field of Classification Search
CPC ............................ G01N 33/241; G01N 13/00
See application file for complete search history.

(56) References Cited

U.S. PATENT DOCUMENTS

| | | | |
|---|---|---|---|
| 7,082,812 B2 * | 8/2006 | Lenormand | G01N 15/0826 73/38 |
| 7,319,332 B2 * | 1/2008 | Lenormand | G01N 33/241 324/376 |
| 7,472,588 B2 * | 1/2009 | Slavin | G01N 15/08 324/376 |

(Continued)

FOREIGN PATENT DOCUMENTS

| CN | 104568699 A | * | 4/2015 |
|---|---|---|---|
| CN | 107807224 A | | 3/2018 |

(Continued)

*Primary Examiner* — John Fitzgerald (57) ABSTRACT

An experimental device for carbon dioxide imbition, diffusion and oil discharge in a tight oil reservoir includes: a multistage rock core holder connected with a confining pressure pump and including a pair of connecting holes arranged at an upper end and a lower end thereof with an oil filler pipe connecting therebetween, a crude oil injection device and a recovery device respectively connected to the upper and lower ends, an intermediate container connected to both a high-pressure cylinder and an injection pump, a return pressure pump, a collection device and a control system. A plurality of rows of openings is arranged at a side of the multistage rock core holder to act as a gas inlet connected with the intermediate container via a pipeline, and a gas outlet connected with the recovery device; heating layers are arranged at inner walls of the multistage rock core holder and the intermediate container.

5 Claims, 9 Drawing Sheets

(56) References Cited

U.S. PATENT DOCUMENTS

| | | | | |
|---|---|---|---|---|
| 8,950,252 | B2* | 2/2015 | Haggerty | G01N 33/24 |
| | | | | 73/152.07 |
| 9,835,762 | B2* | 12/2017 | Pairoys | G01N 27/041 |
| 9,989,512 | B2* | 6/2018 | Haggerty | E21B 49/00 |
| 9,995,136 | B2* | 6/2018 | Brooks | E21B 49/02 |
| 10,133,832 | B2* | 11/2018 | Burghardt | G06F 30/20 |
| 10,260,336 | B2* | 4/2019 | Smith | G01N 1/4022 |
| 10,301,936 | B2* | 5/2019 | Westacott | E21B 43/16 |
| 10,365,202 | B2* | 7/2019 | Ramakrishnan | G01N 15/088 |
| 10,466,153 | B2* | 11/2019 | Gupta | G01N 33/24 |
| 2018/0306031 | A1* | 10/2018 | Smith | G01N 3/40 |

FOREIGN PATENT DOCUMENTS

| | | | |
|---|---|---|---|
| CN | 108507919 A | | 9/2018 |
| CN | 109838218 A | | 6/2019 |
| CN | 109883917 A | | 6/2019 |
| CN | 210322723 U | * | 4/2020 |

* cited by examiner

EXPERIMENTAL DEVICE FOR CARBON DIOXIDE IMBITION, DIFFUSION AND OIL DISCHARGE IN TIGHT OIL RESERVOIR

1. Cross-Reference To Related Application

This application claims the benefit of priority from Chinese Patent Application No. 201911420943.9 entitled "EXPERIMENTAL DEVICE FOR CARBON DIOXIDE IMBITION, DIFFUSION AND OIL DISCHARGE IN TIGHT OIL RESERVOIR" and filed on Dec. 31, 2019, the content of which is hereby incorporated by reference in its entirety by reference.

BACKGROUND

2. Technical Field

The present disclosure generally relates to a technical field of oil and gas field development, in particular to an experimental device, and specifically relates to an experimental device for carbon dioxide imbition, diffusion and oil discharge in a tight oil reservoir.

3. Description of Related Art

With the development of unconventional oil and gas fields in China, tight oil and gas resources have become a key research object of domestic oil development. Due to characteristics of low porosity and low permeability of tight oil reservoirs, conventional water injection ways can't effectively supplement formation capacity, and many tight oil production areas in China are water-scarce areas so that it is difficult to provide large amounts of water. Therefore, how to improve a recovery efficiency of tight reservoirs is a key problem needed to be solved urgently. Carbon dioxide is a gas with high solubility in oil and water, when the carbon dioxide is dissolved in large quantities in crude oil, under an action of the carbon dioxide, a volume of the crude oil can be expanded, viscosity of the crude oil can be decreased, and interfacial tension between oil and water can also be reduced. Compared with other flooding technologies, the carbon dioxide flooding way has many advantages, such as having a wide application range, a low cost of oil flooding and significant improvement of oil recovery. For tight reservoirs with natural fractures or artificial fractures, the carbon dioxide gas flooding way can effectively supplement formation capacity and improve oil recovery. Injected fluid can enter the matrix from the fracture through imbition or diffusion, so that the matrix crude oil can be discharged to the fracture. Therefore, an interaction of the injected fluid and the crude oil between the tight matrix and the fracture is a core factor to affect the oil recovery. After many years of development, the carbon dioxide flooding way, as an increasingly mature oil recovery technology, has been widely concerned by countries around the world.

Due to high costs of field experiments in the oil industry, most of the experiments need to be simulated by computers and be pre-studied by experimental equipments. At present, there are no special devices for a dialysis and discharge test of the carbon dioxide in tight oil reservoirs. For example, patent No. CN 201910069483.3 discloses an experiment device used for a carbon dioxide dialysis and oil discharge experiment, however, such structure is only suitable for a single-layer oil well, most of actual perforations are stratified and provide multilayer fracturing fractures, so that its crude oil dialysis model is more complex.

SUMMARY

The technical problems to be solved: in view of the shortcomings of the related art, the present disclosure relates to an experimental device for carbon dioxide imbition, diffusion and oil discharge in a tight oil reservoir which can effectively improve real simulation of complex well conditions by further improving conventional experimental devices in order to provide some references for an enhanced oil recovery technology in the tight oil reservoir.

The technical solution adopted for solving technical problems of the present disclosure is:

an experimental device for carbon dioxide imbition, diffusion and oil discharge in a tight oil reservoir according to an embodiment of the present disclosure includes a multistage rock core holder with a rock sample and a proppant layer being installed therein, a crude oil injection device, a recovery device, an intermediate container, a high-pressure cylinder, an injection pump, a confining pressure pump connected with the multistage rock core holder, a return pressure pump, a collection device and a control system, an oil filler pipe connected between an upper end and a lower end of the multistage rock core holder; the crude oil injection device connected to a top portion of the oil filler pipe, the recovery device connected to a bottom portion of the oil filler pipe, and an outlet formed at a middle portion of the oil filler pipe; a plurality of rows of openings formed at a side of the multistage rock core holder to be acted as gas inlets and gas outlets, each row of the gas inlet and the gas outlet matched with each other and arranged in a same horizontal plane; the high-pressure cylinder and the injection pump respectively connected to the intermediate container, and the gas inlet connected to the collection device; each of the multistage rock core holder and the intermediate container including a heating layer respectively connected with a heating wire, and then the two heating wires converge to a same heating wire and connected to the control system;

the high-pressure pump connected to the intermediate container via a first pipeline with a first valve being formed thereof, the gas inlet connected to the intermediate container via a second pipeline with a second valve being formed thereof, the crude oil injection device connected to the multistage rock core holder via a third pipeline with a third valve being formed thereof, the recovery device connected to the multistage rock core holder via a fourth pipeline with a fourth valve being formed thereof, the gas outlet connected to the return pressure pump via a fifth pipeline with a fifth valve being formed thereof, the confining pressure pump connected to the multistage rock core holder via a sixth pipeline with a sixth valve being formed thereof;

the multistage rock core holder including an outer cylinder with both the gas inlet and the gas outlet being arranged thereon, an upper plugging member and a lower plugging member respectively formed on the upper end and the lower end of the multistage rock core holder, the upper and lower plugging members being disk structures with a lug boss being formed in a middle thereof, an outer diameter of the lug boss same as an inner diameter of the outer cylinder, a flange extending outwardly from a top end and a bottom end of the outer cylinder, respectively, and each of the upper plugging member and the lower plugging member including a hole formed at their respective edges for corresponding to the flange, a fixing bolt received in the hole to fixedly connect the upper and lower plugging members and the outer cylinder, and a sealing recess arranged on the flange and a sealing ring received in the sealing recess;

each of the upper plugging member and the lower plugging member including a connecting hole arranged on a corresponding middle portion thereof, the oil filler pipe placed in the connecting hole and the sealing recess arranged in the connecting hole, the sealing ring received in the sealing recess for sealing both the connecting hole and the oil filler pipe;

the oil filler pipe including a barrel-configuration inner pipe and a barrel-configuration outer pipe, the outer pipe including a stop ring extending inwardly from an upper portion thereof, both the crude oil injection device and the recovery device hermetically connected with an inner wall of the inner pipe; the sealing recess arranged on the top and the outside of the bottom of the inner pipe, and a sliding seal ring arranged in the sealing recess for hermetically sealing the inner pipe and the outer pipe;

a plurality of inner oil outlets arranged on the inner pipe and a plurality of outer oil outlets arranged on the outer pipe and corresponding to the plurality of inner oil outlets; and a plurality of inner oil discharge holes arranged on the bottom of the inner pipe, and a plurality of outer oil discharge holes arranged on a lower portion of the outer pipe, the outer oil discharge hole and the inner oil discharge hole arranged in a staggered form when the inner oil outlet aligned with the outer oil outlet, and at this time, the outer oil discharge hole higher than the inner oil discharge hole along an axis direction of the oil filler pipe so that the sliding seal ring is formed between the outer oil discharge hole and the inner oil discharge hole; while, the outer oil discharge hole connected with the inner oil discharge hole when the outer pipe moves downward until the stop ring is abutted against the top of the inner pipe.

Wherein the collection device includes a gas collection device and the crude oil collection device arranged below the gas collection device, and both the gas collection device and the crude oil collection device connected to the return pressure pump via the same pipeline converged by their respective pipelines.

Wherein the gas collection device includes a cylinder portion, with a fixing structure, connected to the return pressure pump, and a telescopic portion, the telescopic portion is a corrugated pipe and a glass shielding arranged outside the corrugated pipe, a scale set on the glass shielding, and the glass shielding fitted with the outer of the corrugated pipe so as to ensure the corrugated pipe to move vertically up and down.

Wherein a one-way valve is set in an entrance section of the gas collection device.

Wherein the experimental device further includes a plurality of multistage rock core holders arranged in series, a plurality of outer cylinders connected together by fixing bolts, the upper plugging member arranged at the top end of the uppermost outer cylinder, and the lower plugging member is arranged at the bottom end of the lowermost outer cylinder.

The present disclosure provides the advantages as below.

1. By setting up the multistage rock core holder, a plurality of rock samples and proppant layers can be set in one rock core holder so as to more realistically simulate a reservoir environment after perforation fracturing.

2. The upper plugging member and the lower plugging member are respectively arranged at the upper end and the lower end of the multistage rock core holder are set as detachable structures so as to connect a plurality of multistage rock core holders, which can simulate more-layers conditions.

3. The oil filler pipe is provide with a specific structure so that crude oil can release from the middle of the rock core, thereby the rock core can be better saturated; furthermore, the oil filler pipe is provided as an internal structure so that oil injection and oil discharge can be completed in a same oil filler pipe, thereby avoiding influence on structure strengths and increase sealing difficulty due to too many holes arranged in the multistage rock core holder to respectively inject and discharge oil.

The element labels according to the embodiment of the present disclosure shown as below:

multistage rock core holder 1, crude oil injection device 2, oil filler pipe 3, recovery device 4, heating wire 5, intermediate container 6, high-pressure gas cylinder 7, injection pump 8, confining pressure pump 9, return pressure pump 10, gas collection device 11, crude oil collection device 12, proppant layer 13, rock sample 14, control system 15, first pipeline 16, second pipeline 16a, third pipeline 16b, fourth pipeline 16c, fifth pipeline 16d, sixth pipeline 16e, seventh pipeline 16f, first valve 17, second valve 17a, third valve 17b, fourth valve 17c, fifth valve 17d, sixth valve 17e, seventh valve 17f, collection device 18, connecting hole 20, opening 100, outer cylinder 101, lug boss 1011, flange 1012, edge 1015, hole 1016, upper plugging member 102, sealing ring 103, sealing recess 1031, fixing bolt 104, lower plugging member 105, gas inlet 106, gas outlet 107, heating layer 108, confining pressure entrance 109, cylinder portion 1101, telescopic portion 1102, glass shielding 1103, scale 1104, check valve 1105, entrance section 1106, inner pipe 301, outlet 3010, inner oil outlet 3011, inner oil discharge hole 3012, top 3013, inner wall 3014, bottom 3015, outside 3016, outer pipe 302, sliding seal ring 303, outer oil outlet 3021, stop ring 3022, outer oil discharge hole 3023, upper portion 3024, lower portion 3025.

DETAILED DESCRIPTION

Reference will now be made in detail to embodiments, examples of which are illustrated in the accompanying drawings.

A first embodiment of the present disclosure:

Referring to FIGS. 1-9, an experimental device for carbon dioxide imbition, diffusion and oil discharge in a tight oil reservoir includes a multistage rock core holder 1, a crude oil injection device 2, a recovery device 4, an intermediate container 6, a high-pressure cylinder 7, an injection pump 8, a confining pressure pump 9, a return pressure pump 10, a collection device 18 and a control system 15. Both a rock sample 14 and a proppant layer 13 are installed in the multistage rock core holder 1. A pair of connecting holes 20 is respectively arranged on an upper end and a lower end of the multistage rock core holder 1, and an oil filler pipe 3 is connected between the upper end and the lower end of the multistage rock core holder 1. The high-pressure cylinder 7 and the injection pump 8 are respectively connected to the intermediate container 6. The high-pressure pump 7 is connected to the intermediate container 6 via a first pipeline 16 with a first valve 17 being formed thereof. The crude oil injection device 2 is connected to the multistage rock core holder 1 via a third pipeline 16b with a third valve 17b being formed thereof, and the recovery device 4 is connected to the multistage rock core holder 1 via a fourth pipeline 16c with a fourth valve 17c being formed thereof. An outlet 3010 is formed at a middle portion of the oil filler pipe 3. Three rows of openings 100 are formed at a side of the multistage rock core holder 1 to be acted as gas inlets 106 and gas outlets 107. Each row of the gas inlet 106 and the gas outlet 107 are matched with each other and arranged in a same horizontal plane. Specifically, each row of the openings 100 shall be provided with at least two holes 100 acted as the gas inlet 106 and the gas outlet 107, respectively. If the number of each row of the openings 100 is more than two, the gas inlet 106 and the gas outlet 107 should be allocated as required, but the gas inlet 106 and the gas outlet 107 of each row should be arranged in a same vertical line. The gas inlet 106 is connected to the intermediate container 6 via a second pipeline 16a with a second valve 17a being formed thereof, and the gas outlet 107 is connected to the collection device 18 via the return pressure pump 10. The gas outlet 107 is connected to the return pressure pump 10 via a fifth pipeline 16d with a fifth valve 17d being formed thereof, and the multistage rock core holder 1 is connected to the confining pressure pump 9 via a sixth pipeline 16e with a sixth valve 17e being formed thereof. A heating layer 108 is arranged at an inner wall of each of the multistage rock core holder 1 and the intermediate container 6, respectively. Specifically, the heating layer 108 is arranged at the full inner wall of the intermediate container 6, while, the heating layer 108 is only arranged at an inner side of the multistage rock core holder 1, rather than the upper end and the lower end. The heating layers 108 of the multistage rock core holder 1 and the intermediate container 6 are respectively connected with a heating wire 5, and then the two heating wires 5 are converged to a same heating wire and connected to the control system 15. The control system 15 includes a power supply and an industrial computer for controlling to open and close the valve and heating temperature in the experiment.

Figure 7:
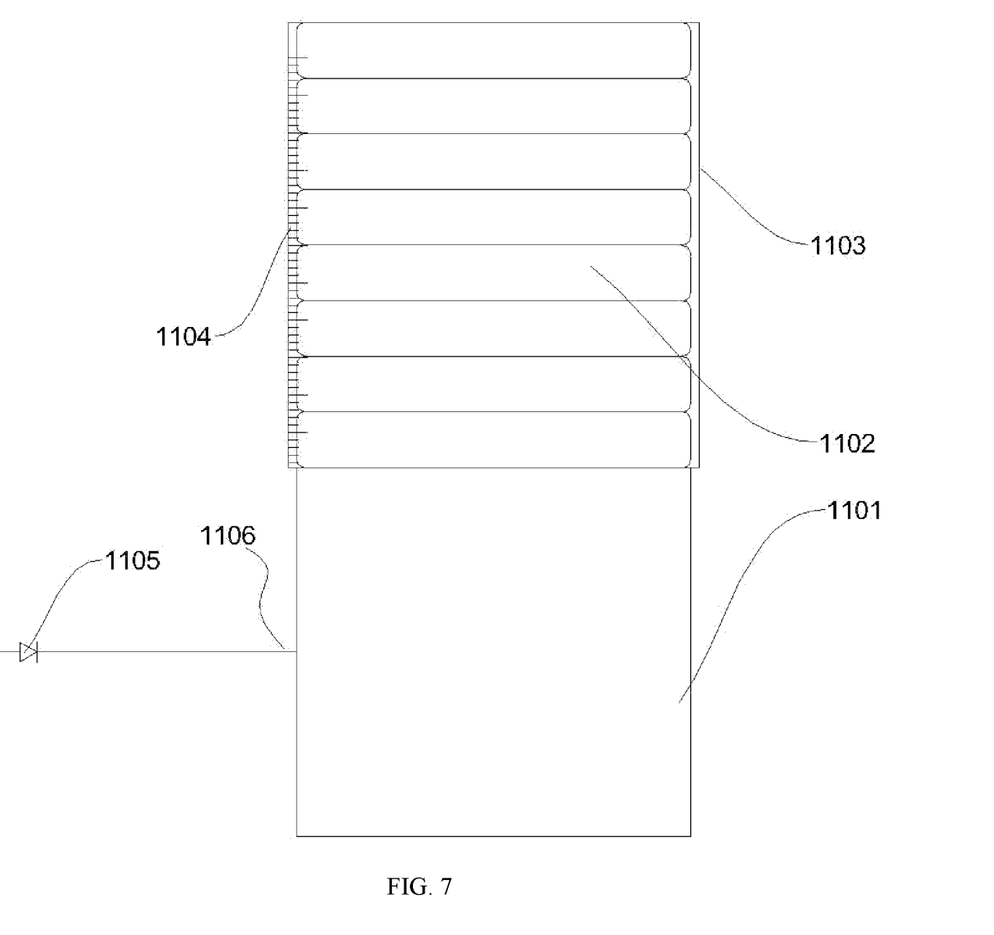
FIG. 7 is a schematic view of a gas collection device of the experimental device of the present disclosure.

According to a preferred embodiment of the present disclosure, the collection device 18 is connected to the return pressure pump 10 via a seventh pipeline 16f with a seventh valve 17f being formed thereof, and includes a gas collection device 11 and the crude oil collection device 12 arranged below the gas collection device 11. Both the gas collection device 12 and the crude oil collection device 11 are connected to the return pressure pump 10 via a same pipeline converged by their respective pipelines 16g. The gas collection device 11 includes a cylinder portion 1101 and a telescopic portion 1102. The cylinder portion 1101 is a fixing structure and connected to the return pressure pump 10, and the telescopic portion 1102 is a corrugated pipe and a glass shielding 1103 arranged outside the corrugated pipe. A scale 1104 is set on the glass shielding 1103, and the glass shielding 1103 is fitted with the outer of the corrugated pipe so as to ensure the corrugated pipe to move vertically up and down. The corrugated pipe has a constant initial position and is filled with liquid. Before air is entered, no gas is received in the gas collection device 11, in this way, a volume of recovery gas can be determined by observing a rising height of the corrugated pipe. A one-way valve 1105 is set in an entrance section 1106 of the gas collection device 11 so as to avoid gas to reverse overflow.

Figure 1:
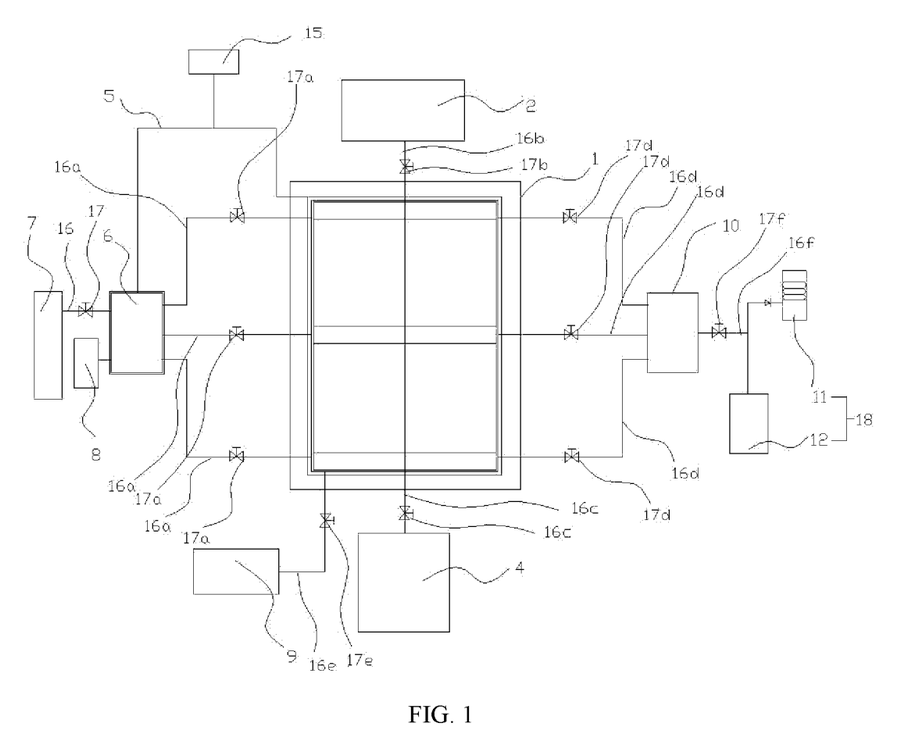
FIG. 1 is a schematic view of an experimental device for carbon dioxide imbition, diffusion and oil discharge in a tight oil reservoir in accordance with an embodiment of the present disclosure.
Figure 2:
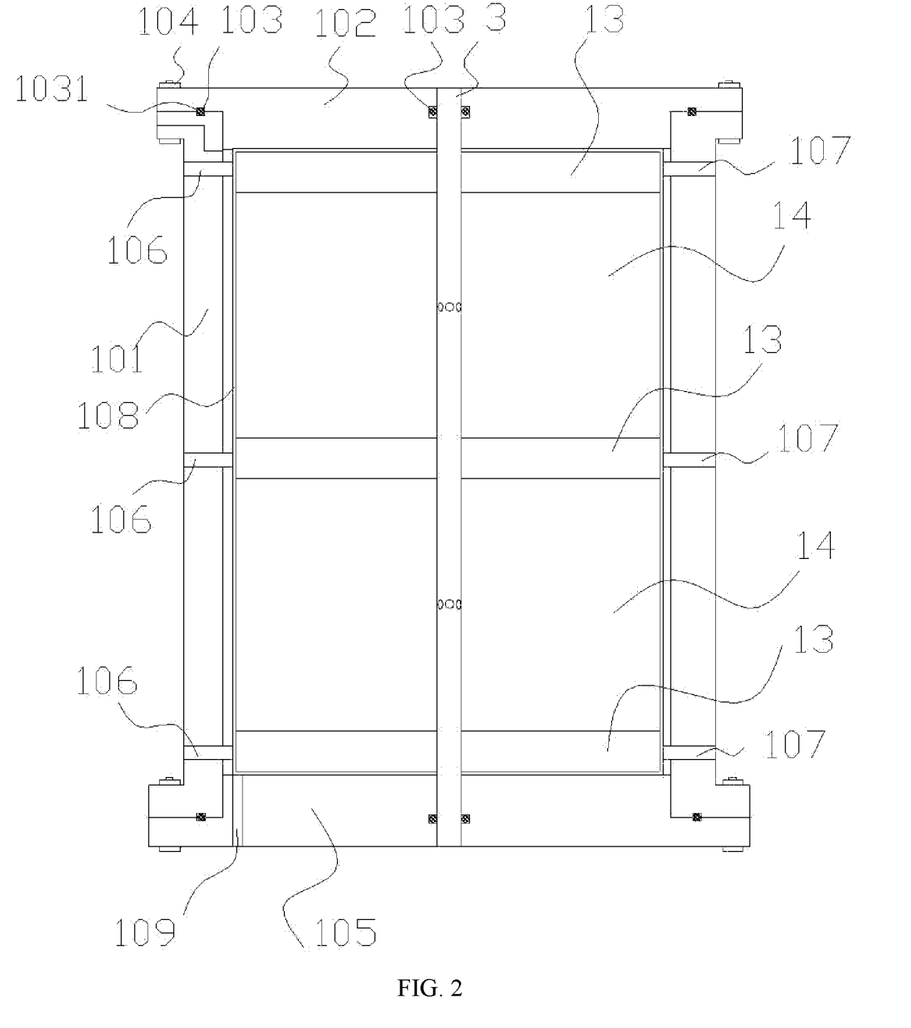
FIG. 2 is a partial inner schematic view of a multistage rock core holder of the experimental device of the present disclosure.
Figure 8:
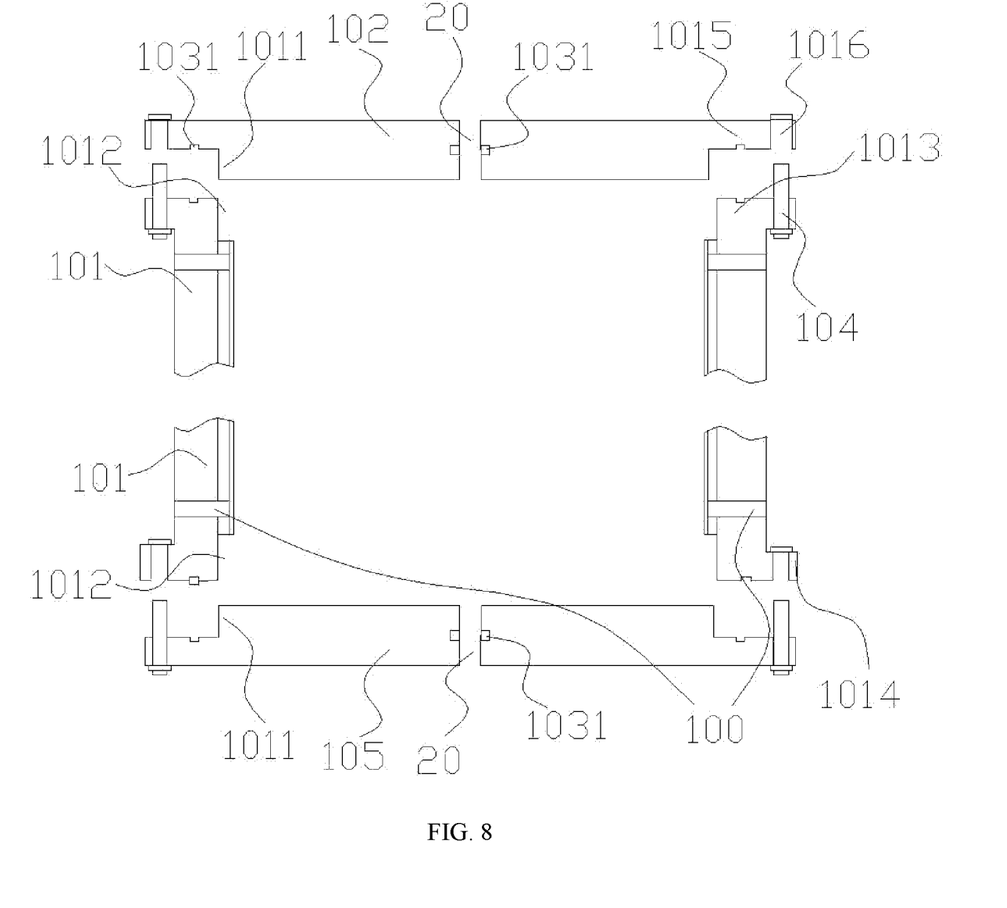
FIG. 8 is a schematic view of an upper plugging member, a lower plugging member and an outer cylinder of the multistage rock core holder of the experimental device of the present disclosure.
Figure 9:
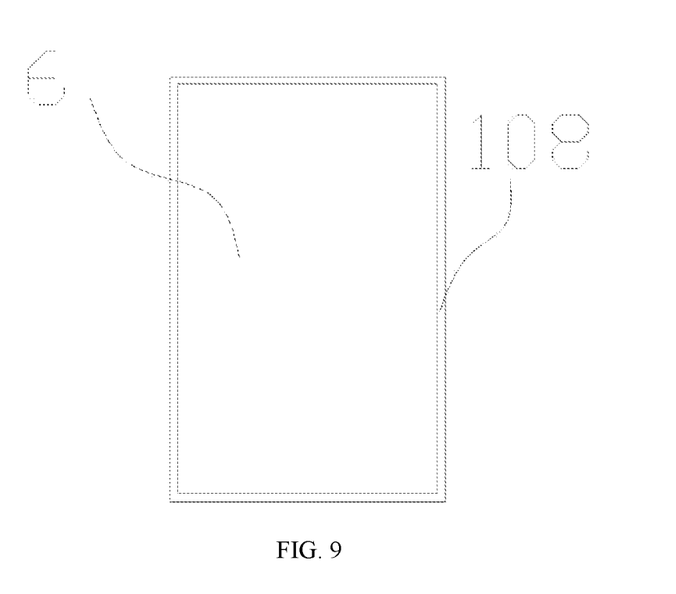
FIG. 9 is an enlarged schematic view of an intermediate container of the experimental device of the present disclosure.

According to a preferred embodiment of the present disclosure, referring to FIG. 2, the multistage rock core holder 1 includes an outer cylinder 101, an upper plugging member 102 and a lower plugging member 105. Both the gas inlet 106 and the gas outlet 107 are arranged on the outer cylinder 101, both the upper plugging member 102 and the lower plugging member 105 are arranged on a top end and a bottom end of the outer cylinder 101, respectively. Both the upper plugging member 102 and the lower plugging member 105 are disk structures with a lug boss 1011 being formed in a middle thereof, and an outer diameter of the lug boss 1011 is same as an inner diameter of the outer cylinder 101. A flange 1012 is extended outwardly from the top end and the bottom end of the outer cylinder 101, respectively, and each of the upper plugging member 102 and the lower plugging member 105 includes a hole 1016 formed at their respective edges 1015 for corresponding to the flange 1012. A fixing bolt 104 is received in the hole 1016 to fixedly connect the upper and lower plugging members 102, 105 and the outer cylinder 101, and a sealing recess 1031 arranged on the flange 1012 and a sealing ring 103 received in the sealing recess 1031. Each of the upper plugging member 102 and the lower plugging member 105 includes the connecting hole 20 arranged on a corresponding middle portion thereof, the oil filler pipe 3 placed in the connecting hole 20 and the sealing recess 1031 arranged in the connecting hole 20, the sealing ring 103 received in the sealing recess 1031 for sealing both the connecting hole 20 and the oil filler pipe 3.

Referring to FIGS. 3-6, the oil filler pipe 3 includes a barrel-configuration inner pipe 301 and a barrel-configuration outer pipe 302. The outer pipe 302 includes a stop ring 3022 extending inwardly from an upper portion 3024 thereof, both the crude oil injection device 2 and the recovery device 4 are hermetically connected with an inner wall 3014 of the inner pipe 301. The sealing recess 1031 is arranged on the top 3013 and the outside 3016 of the bottom 3015 of the inner pipe 301, and a sliding seal ring 303 arranged in the sealing recess 1031 for hermetically sealing the inner pipe 301 and the outer pipe 302. A plurality of inner oil outlets 3011 is arranged on the inner pipe 301 and a plurality of outer oil outlets 3021 is arranged on the outer pipe 302 and corresponding to the plurality of inner oil outlets 3011. A plurality of inner oil discharge holes 3012 is arranged on the bottom 3015 of the inner pipe 301, and a plurality of outer oil discharge holes 3023 is arranged on a lower portion 3025 of the outer pipe 302. The outer oil discharge hole 3023 and the inner oil discharge hole 3012 are arranged in a staggered form when the inner oil outlet 3011 is aligned with the outer oil outlet 3021. At this time, the outer oil discharge hole 3023 is higher than the inner oil discharge hole 3012 along an axis direction of the oil filler pipe 3 so that the sliding seal ring 303 is formed between the outer oil discharge hole 3023 and the inner oil discharge hole 3012. While, the outer oil discharge hole 3023 is connected with the inner oil discharge hole 3012 when the outer pipe 302 moves downward until the stop ring 3022 is abutted against the top 3013 of the inner pipe 301.

Figure 3:
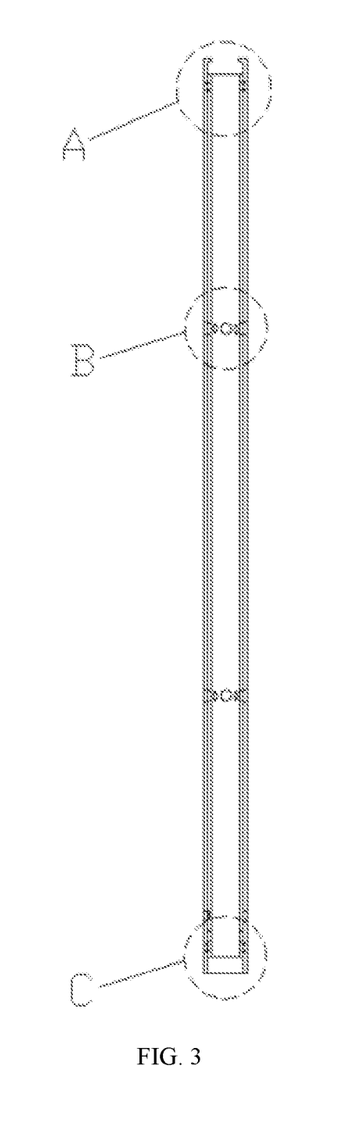
FIG. 3 is a schematic view of an oil filler pipe of the experimental device of the present disclosure.
Figure 4:
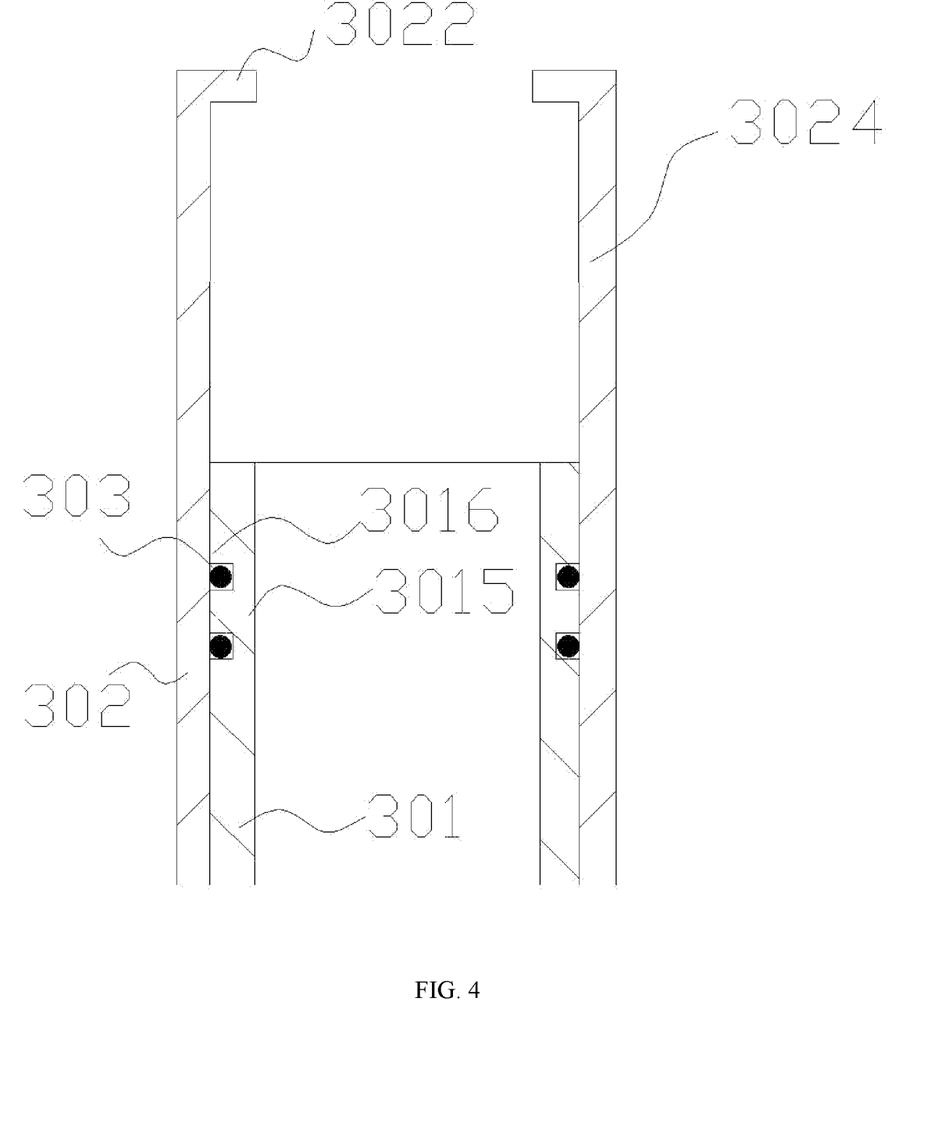
FIG. 4 is an enlarged schematic view of part A of FIG. 3.
Figure 5:
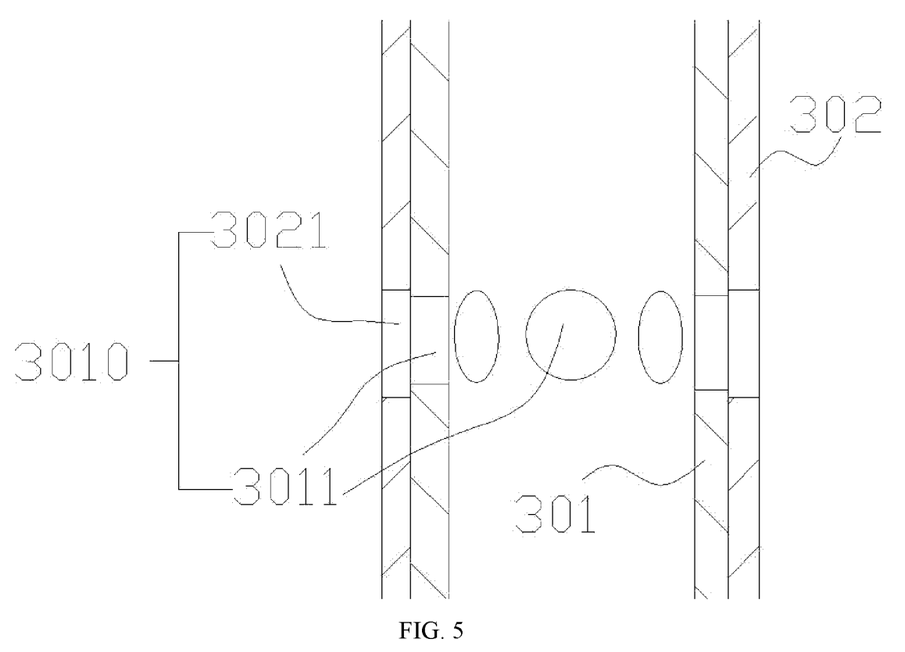
FIG. 5 is an enlarged schematic view of part B of FIG. 3.
Figure 6:
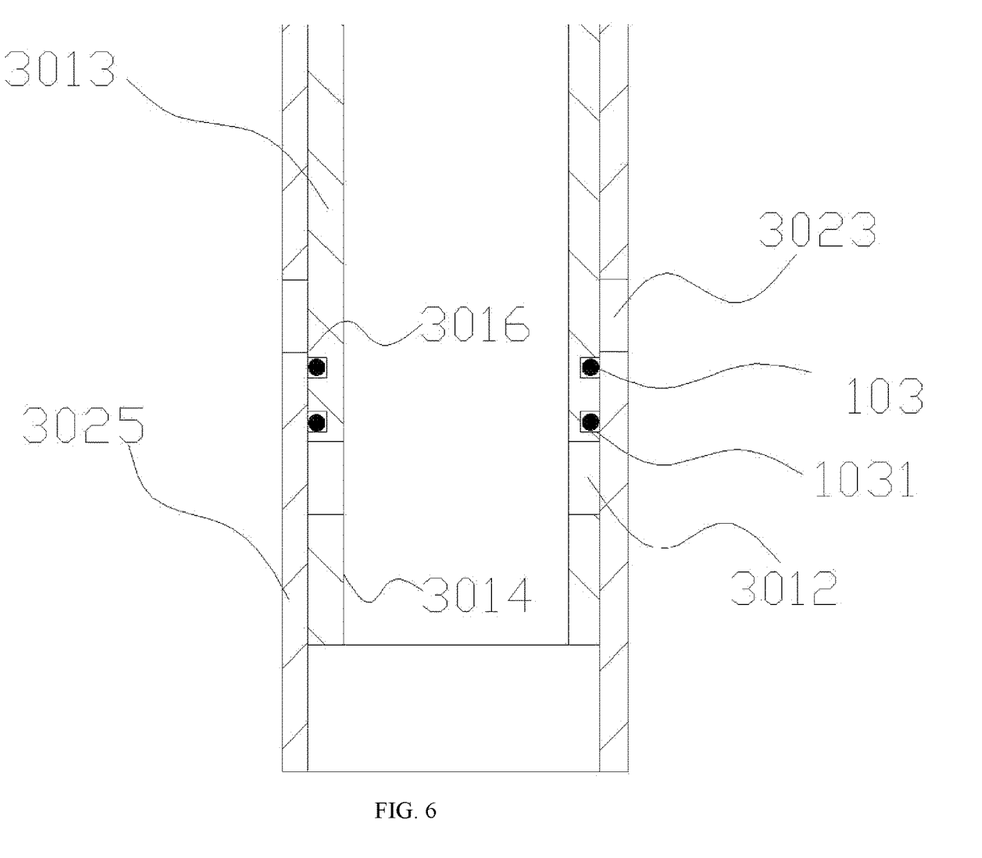
FIG. 6 is an enlarged schematic view of part C of FIG. 3.

In an embodiment of the present disclosure, an installation method is as follows: the proppant layer used is a proppant actually used for fracturing, and the rock sample 14 is a rock sample with a hole being formed in the middle thereof. After the lower plugging member 105 arranged at the lower end of the multistage rock core holder 1 is completely fixed, inserting the oil filler pipe 3, putting in one layer of proppant layer and then one rock sample with holes, and then laying a second layer of proppant layer and putting in a second rock sample with holes; finally, laying a third layer of proppant layer, and then covering the upper plugging member 102.

A specific usage is as follows:

Step S1: Cleaning and drying pipelines of the experimental device, connecting the installed multistage rock core holder 1 with other devices, setting a working procedure and a process environment of the control system, and connecting the experimental device and checking air tightness of the experimental device;

Step S2: Injecting crude oil into the rock core through the oil filler pipe 3, with the inner oil discharge hole 3011 being connected with the outer oil discharge hole 3021, after the crude oil is saturated, moving the outer pipe 302 downwardly to isolate the inner oil discharge hole 3011 and the outer oil discharge hole 3021 until the inner oil discharge hole 3011 and the outer oil discharge hole 3021 are not connected with each other, and then controlling the environment through the confining pressure pump 9 and the heating layer 108 to simulate an actual situation of the formation;

Step S3: Opening the first valve 17 positioned after the high-pressure cylinder 7 and the second valve 17a of the second line 16a where a selected gas inlet 106 is located, and driving the injection pump 8 to feed the carbon dioxide, and then closing the second valve 17a for soaking the gas;

Step S4: Closing the first valve 17 of the high-pressure cylinder 7 after the soaking time is over, and opening the return pressure pump 10 to drive oil to the return pressure pump 10 by the injection pump 8, and then into the gas collection device 11 and the crude oil collection device 12 until no crude oil can be driven, and finally recording a volume of the crude oil and a volume of the gas;

Step S5: If necessary, repeating the steps S2-S4 to determine an average parameter;

Step S6: Cleaning the experimental device for a next use.

A second embodiment of the present disclosure:

The experimental device further includes a plurality of multistage rock core holders 1 arranged in series, and a plurality of outer cylinders 101 is connected together by fixing bolts 104. The upper plugging member 102 is arranged at the top end of the uppermost outer cylinder 101, and the lower plugging member 105 is arranged at the bottom end of the lowermost outer cylinder 101. Similarly, the gas inlet 106 and the gas outlet 107 can be connected to the intermediate container 6 and the return pressure pump 10, respectively. If it is required, a plurality of intermediate containers 6 and a plurality of return pressure pumps 10 can be set, and other devices can also be set accordingly. Because the present disclosure is to simulate more real formation environments, in some cases, some gas inlets 106 and some gas outlets 107 can be closed so as to realistically simulate fracturing conditions at different intervals.

The foregoing description is not in any form a limitation to the present disclosure. Although the features and elements of the present disclosure are described as embodiments in particular combinations, but not intended to limit the protection scope of the present disclosure, each feature or element can be used alone or in other various combinations within the principles of the present disclosure to the full extent indicated by the broad general meaning of the terms in which the appended claims are expressed. Any variation or replacement made by one of ordinary skill in the related art without departing from the spirit of the present disclosure shall fall within the protection scope of the present disclosure.

What is claimed is:

1. An experimental device for carbon dioxide imbition, diffusion and oil discharge in a tight oil reservoir comprising:

a multistage rock core holder with a rock sample and a proppant layer being installed therein, a crude oil injection device, a recovery device, an intermediate container, a high-pressure cylinder, an injection pump, a confining pressure pump connected with the multistage rock core holder, a return pressure pump, a collection device and a control system, an oil filler pipe connected between an upper end and a lower end of the multistage rock core holder; the crude oil injection device connected to a top portion of the oil filler pipe, the recovery device connected to a bottom portion of the oil filler pipe, and an outlet formed at a middle portion of the oil filler pipe; a plurality of rows of openings formed at a side of the multistage rock core holder to be acted as gas inlets and gas outlets, each row of the gas inlet and the gas outlet matched with each other and arranged in a same horizontal plane; the high-pressure cylinder and the injection pump respectively connected to the intermediate container, and the gas inlet connected to the collection device; each of the multistage rock core holder and the intermediate container comprising a heating layer respectively connected with a heating wire, and then the two heating wires converge to a same heating wire and connected to the control system;

the high-pressure pump connected to the intermediate container via a first pipeline with a first valve being formed thereof, the gas inlet connected to the intermediate container via a second pipeline with a second valve being formed thereof, the crude oil injection device connected to the multistage rock core holder via a third pipeline with a third valve being formed thereof, the recovery device connected to the multistage rock core holder via a fourth pipeline with a fourth valve being formed thereof, the gas outlet connected to the return pressure pump via a fifth pipeline with a fifth valve being formed thereof, the confining pressure pump connected to the multistage rock core holder via a sixth pipeline with a sixth valve being formed thereof;

the multistage rock core holder comprising an outer cylinder with both the gas inlet and the gas outlet being arranged thereon, an upper plugging member and a lower plugging member respectively formed on the upper end and the lower end of the multistage rock core holder, the upper and lower plugging members being disk structures with a lug boss being formed in a middle thereof, an outer diameter of the lug boss same as an inner diameter of the outer cylinder, a flange extending outwardly from a top end and a bottom end of the outer cylinder, respectively, and each of the upper plugging member and the lower plugging member comprising a hole formed at their respective edges for corresponding to the flange, a fixing bolt received in the hole to fixedly connect the upper and lower plugging members and the outer cylinder, and a sealing recess arranged on the flange and a sealing ring received in the sealing recess;

each of the upper plugging member and the lower plugging member further comprising a connecting hole arranged on a corresponding middle portion thereof, the oil filler pipe placed in the connecting hole and the sealing recess arranged in the connecting hole, the sealing ring received in the sealing recess for sealing both the connecting hole and the oil filler pipe;

the oil filler pipe comprising a barrel-configuration inner pipe and a barrel-configuration outer pipe, the outer pipe comprising a stop ring extending inwardly from an upper portion thereof, both the crude oil injection device and the recovery device hermetically connected with an inner wall of the inner pipe; the sealing recess arranged on the top and the outside of the bottom of the inner pipe, and a sliding seal ring arranged in the sealing recess for hermetically sealing the inner pipe and the outer pipe;

a plurality of inner oil outlets arranged on the inner pipe and a plurality of outer oil outlets arranged on the outer pipe and corresponding to the plurality of inner oil outlets; and a plurality of inner oil discharge holes arranged on the bottom of the inner pipe, and a plurality of outer oil discharge holes arranged on a lower portion of the outer pipe, the outer oil discharge hole and the inner oil discharge hole arranged in a staggered form so that the inner oil outlet aligned with the outer oil outlet, and at this position, the outer oil discharge hole is located higher than the inner oil discharge hole along a longitudinal axis direction of the oil filler pipe so that the sliding seal ring is formed between the outer oil discharge hole and the inner oil discharge hole; while, the outer oil discharge hole connected with the inner oil discharge hole when the outer pipe moves downward until the stop ring is abutted against the top of the inner pipe.

2. The experimental device for carbon dioxide imbition, diffusion and oil discharge in a tight oil reservoir as claimed in claim 1, wherein the experimental device further comprises a plurality of multistage rock core holders arranged in series, a plurality of outer cylinders connected together by fixing bolts, the upper plugging member arranged at the top end of the uppermost outer cylinder, and the lower plugging member is arranged at the bottom end of the lowermost outer cylinder.

3. The experimental device for carbon dioxide imbition, diffusion and oil discharge in a tight oil reservoir as claimed in claim 1, wherein the collection device comprises a gas collection device and the crude oil collection device arranged below the gas collection device, and both the gas collection device and the crude oil collection device are connected to the return pressure pump via the same pipeline converged by their respective pipelines.

4. The experimental device for carbon dioxide imbition, diffusion and oil discharge in a tight oil reservoir as claimed in claim 3, wherein the gas collection device comprises a cylinder portion, with a fixing structure, connected to the return pressure pump, and a telescopic portion, the telescopic portion is a corrugated pipe and a glass shielding arranged outside the corrugated pipe, a scale set on the glass shielding, and the glass shielding fitted with the outer of the corrugated pipe, thus configuring to ensure the corrugated pipe to move vertically up and down.

5. The experimental device for carbon dioxide imbition, diffusion and oil discharge in a tight oil reservoir as claimed in claim 4, wherein a one-way valve is set in an entrance section of the gas collection device.

* * * * *